United States Patent [19]

Miller

[11] Patent Number: 5,227,159
[45] Date of Patent: Jul. 13, 1993

[54] ANTI-IDIOTYPE ANTIBODIES REACTIVE WITH SHARED IDIOTOPES EXPRESSED BY B CELL LYMPHOMAS AND AUTOANTIBODIES

[76] Inventor: Richard A. Miller, 8 Ohlone, Portola Valley, Calif. 94025

[21] Appl. No.: 898,246

[22] Filed: Jun. 12, 1992

Related U.S. Application Data

[63] Continuation of Ser. No. 467,405, Jan. 22, 1990, abandoned, which is a continuation-in-part of Ser. No. 304,745, Jan. 31, 1989, abandoned.

[51] Int. Cl.$^5$ .................. A61K 39/395; C07K 15/28; C12N 5/20
[52] U.S. Cl. .................. 424/85.8; 530/387.2; 530/388.73; 530/388.8; 435/70.21; 435/172.2; 435/240.27; 935/104; 935/107
[58] Field of Search .................. 424/85.8; 530/387.2, 530/387.3, 388.73, 388.8; 435/70.21, 172.2, 240.27

[56] References Cited

U.S. PATENT DOCUMENTS 4,661,586 4/1987 Levy et al. .................. 530/387

FOREIGN PATENT DOCUMENTS 0141783 5/1985 European Pat. Off. ............ 339/395
0291636 11/1988 European Pat. Off. ............ 39/395
WO 88/09670 12/1988 PCT Int'l Appl. .

OTHER PUBLICATIONS

Miller et al., "Treatment of B-cell Lymphoma With Monoclonal Anti-Idiotype Antibody," *N. Engl. J. Med.* 306:517-522, Mar. 4, 1982.
Meeker et al., "A Clinical Trial of Anti-Idiotype Therapy for B-Cell Malignancy," *Blood* 65:1349-1363, Jun. 1985.
Miller et al., "Shared Idiotypes Expressed by Human B-cell Lymphomas," *N Engl. J. Med.* 321:851-857, Sep. 28, 1989.
Stevenson et al., "Antibodies to Shared Idiotypes as Agents for Analysis and Therapy for Human B cell Tumors," *Blood* 68:430-436, Aug., 1986.

(List continued on next page.)

Primary Examiner—David L. Lacey
Assistant Examiner—Robert D. Budens
Attorney, Agent, or Firm—Kenneth J. Woolcott; Richard P. Burgoon, Jr.

[57] ABSTRACT

B-cell lymphomas express surface immunoglobulin (immunoglobulin) containing unique idiotypic (idiotype) determinants which may be exploited as tumor specific markers. The inventor has produced murine monoclonal antibodies (MAbs) reactive with the idiotype marker derived from 67 patients with low grade, follicular, small cleaved cell lymphoma. Out of 199 monoclonal antibodies, 47 (24%) were found to react with pooled normal human serum immunoglobulin in concentrations ranging from 0.6 $\mu$g/ml to 160 $\mu$g/ml. Of these 40 monoclonal antibodies, 90% cross-reacted with idiotype present in normal serum in levels <50 $\mu$g/ml. Thirty-two of these anti-idiotypes were directed against a shared idiotope expressed on another patient's lymphoma cells. The frequency of shared idiotope expression defined by each antibody ranged from 0.26% to 3.9% of the B-cell lymphomas tested. A panel of five anti-idiotype antibodies reacted with 80% of AIDS associated lymphomas. Based on the reactivity with these monoclonal antibodies, tumors could be grouped into distinct families. In aggregate, these 32 monoclonal antibodies reacted with a total of 108 of 332 B cell lymphoma cases (32.5%), including 35 of 116 follicular, small cleaved cell lymphomas (30%). Many of these anti-shared idiotopes reacted with more than one histopathologic subtype of lymphoma. Anti-idiotypes have been used in B-cell lymphoma diagnosis and therapy. Moreover, applicant has discovered at least seven anti-shared idiotype antibodies that cross react with autoantibodies, e.g., 16.6 and RF. The development of a library of anti-idiotypes reactive with shared idiotopes should facilitate these clinical studies by obviating the need to develop a customized hybridoma for each patient.

12 Claims, 6 Drawing Sheets

OTHER PUBLICATIONS

Pasquali, J-L. A highly conserved determinant on human rheumatoid factor idiotypes defined by a mouse monoclonal antibody. 1983. Eur. J. Immunol. 13:197–201.

Carson, D. A., and Fong, S. A common idiotype on human rheumatoid factors identified by a hybridoma antibody. 1983. Molec. Immunol. 20: 1081–1087.

Perek, Y., et al. Immunotherapy of a murine B cell tumor with antibodies and F(ab')$_2$ fragments against idiotypic determinants of its cell surface IgM. 1983. J. Immunol. 131:1600–1603.

Thielemans, K., et al. Strategies for production of monoclonal anti-iodiotype antibodies against human B cell lymphomas. 1984. J. Immunol. 133:495–501.

Pennell, C. A., et al. Cross-reactive idiotypes and common antigen binding specificities expressed by a series of murine B-cell lymphomas: Etiological implications. Proc. Natl. Acad. Sci. USA 82:3799–3803.

Fox, R. I., et al. Expression of a cross-reactive idiotype on rheumatoid factor in patients with Sjogren's syndrome. 1986. J. Immunol. 136:477–483.

Raychaudhuri, S., et al. Tumor-specific idiotype vaccines: I. Generation and characterization of internal image tumor antigen. 1986. J. Immunol. 137:1743–1749.

Lowder, J. N., et al. Studies on B lymphoid tumors treated with monoclonal anti-idiotype antibodies: Correlation with clinical responses. 1987. Blood 69:199–210.

Kiyotaki, M., et al. Monoclonal anti-id antibodies react with varying proportions of human B lineage cells. 1987. J. Immunol. 138:4150–4158.

Burdette, S., and Schwartz, R. S. Current concepts: Immunology. Idiotypes and idiotypic networks. 1987. New Engl. J. Med. 317:219–224.

Kipps, T. J., et al. Autoantibody-associated kappa light chain variable region gene expressed in chronic lymphocytic leukemia with little or no somatic mutation. 1988. J. Exp. Med. 167:840–852.

Sugano, T., et al. Human monoclonal antibody against glycoproteins of human immunodeficiency virus. 1988. Biochem. Biopyhs. Res. Comm. 155:1105–1112.

Brown, S. L., et al. Treatment of B-cell lymphomas with anti-idiotype antibodies alone and in combination with alpha interferon. 1989. Blood 73:651–661.

Hay, et al. 1976 Clinical Experimental Immunology, 24:396–400 Routine Assay for the Detection of Immune Complexes of Known Immunoglbulin Class Using Solid Phase Clq. s.

ANTI-IDIOTYPE ANTIBODIES REACTIVE WITH SHARED IDIOTOPES EXPRESSED BY B CELL LYMPHOMAS AND AUTOANTIBODIES

REFERENCE TO RELATED APPLICATION

This application is a continuation of U.S. Ser. No. 07/467,405, filed Jan. 22, 1990, now abandoned, which is in turn a continuation-in-part of U.S. Ser. No. 304,745, filed Jan. 31, 1989, now abandoned.

FIELD OF THE INVENTION

The present invention is in the field of immunodiagnosis and immuno-therapy. Specifically, the invention relates to the discovery of antibodies that may be used in the prevention, diagnosis, monitoring, treatment, and amelioration of autoimmune diseases, HIV associated B-cell lymphomas, and B-cell lymphomas generally.

BACKGROUND OF THE INVENTION

The Immune System and Antibody Diversity

Antibodies (immunoglobulins) are produced by the B-cells (B-lymphocytes) of the immune system of animals for the purpose of recognizing and contributing to the elimination of foreign substances found within the host mammal. Any foreign substance, typically but not exclusively a protein, that induces such an antibody response by the host, is termed an antigen. Upon antigen stimulation, mature B-cells differentiate into plasma cells that proliferate and secrete antigen specific antibodies into the serum.

Immunoglobulins are Y-shaped, tetrameric molecules consisting of two relatively long polypeptide chains called heavy (H) chains and two shorter polypeptide chains called light (L) chains. Each pair of arms of the Y-shaped structure has specific antigen binding properties and each arm is referred to as an antigen-binding fragment (Fab region). The tail (or base) of the Y structure is a crystallizable fragment (Fc) that includes the binding site for activating cytolytic activity (the Fc region).

Immunoglobulin molecules possess variable regions that are responsible for their specific antigen recognition. The features that distinguish one immunoglobulin variable region from another are collectively termed the antibody "idiotype," which is derived from the Greek for "private form." In the next step in classification and nomenclature, the variable region idiotypes contain and are defined by a plurality of determinants, termed "idiotopes." These idiotopes consist of three dimensional configurations of various peptides that make up the polypeptide chains of the Fab regions; like foreign protein antigens, each idiotope is immunogenic and capable of eliciting anti-idiotype immune responses (antibodies specific for an individual idiotope or group of idiotopes). (See, e.g., Kunkel, H. G., et al., *Science* 140:1218 (1963); Oudin, J., and Michel, M., *Cr. Acad. Sci.* (Paris) 257:805 (1963).)

The variable region is encoded for by $V_H$, D and $J_H$ gene segments for the heavy chain and $V_L$ and $J_L$ gene segments for the light chain. (See Tonegawa, S., *Nature* 302:575 (1983). It is the combination of these genetic elements that creates distinct antigenic determinants, or idiotopes, within the immunoglobulin variable regions. Idiotopes may be shared (e.g., "public") or not shared (e.g., "private"). These terms and the concept of shared idiotopes are explained below.

An antibody whose formation is stimulated by administration of an antigen can bind the antigen through non-covalent bonds. This binding is postulated to be based on topographic complementarity of the antibody binding site with the binding site of the antigen. (the inventor does not, however, presume any specific means through which such binding may actually occur.) The binding site of the antigen, which is thereby recognized by the antibody, is termed the "epitope" and the binding site on the antibody is termed the "paratope." (Jerne, N., *Ann. Immunol.* (Inst. Pasteur) 125C:373 (1974).) A paratope may serve as an idiotope, i.e., the paratope may stimulate an anti-idiotypic response in which, like the original epitope, the anti-idiotypic antibodies bind to the paratope. If an anti-paratope anti-idiotope antibody structurally mimics the antigen it is called the "internal image" of the antigen. In addition to these anti-paratopic anti-idiotypes that represent the configuration of the original antigen, other anti-idiotypic antibodies define antibody and T-cell receptor idiotopes that participate in the regulation of immune responses. These idiotypes are termed "regulatory idiotypes" and they are not necessarily the internal images of the original antigen. (See, e.g., Burdette, S. and Schwartz, R., *New Eng. J. of Med.* 317:219 (1987).) The utility of internal image anti-idiotypes in immunotherapy has been shown in experimental systems. Internal image anti-idiotypes have been used, for example, as surrogates for antigens in generating specific immune responses against viral, bacterial, and parasitic infections, and cancers. (See, e.g., Herlyn, D., et al., *Science* 232:100 (1986); Raychaudhuri, S., et al., *J. Immunol.* 137:1743 (1986)).

There exists a large number of antibodies that will bind to a particular antigen. There are a few reasons for this diversity. Firstly, there are hundreds of different $V_H$ and $V_L$ gene segments. Different gene segments can be expressed in different combinations for different antigenic binding properties. Secondly, $V_H$ or $V_L$ genes may be combined with different D and J gene segments. Thirdly, different $V_H$ and $V_L$ chains may be combined in different ways. These factors are the cause of the diversity of immunoglobulin expression observed in mammals. Somatic mutations occur in B-cells that further increase diversity.

Even at the epitope level of specificity, the body may produce more than one antibody molecule reactive with that epitope. These antibodies may differ in the constant region or the variable region of the light or heavy chain. Within a species, differences may be seen in the heavy chain constant region. These differences are known as "isotypes" and refer to different immunoglobulin classes and subclasses within the immune system, e.g., IgG1, IgG2, IgG3, IgG4, IgM, IgA1, IgA2, and IgE in humans. These structural differences provide different immunoglobulin molecules with specific effector functions such as ability to fix complement, to increase phagocytosis by macrophages, etc. Within a particular individual's antibody isotype, additional inherited differences in heavy chain constant region structure may occur and are termed "allotypes." The allotypic regions of the heavy chain constant region are derived from genes that are inherited from each of the individual's parents. The differences in antibody molecule seen in the immunoglobulin variable regions are a result of the use of particular $V_H$ and $V_L$ genes by the B-cell as it differentiates into an antibody producing plasma cell. Thus, an antibody reactive with a particular epitope present on an antigen may use different heavy chain constant regions, different light chain constant regions (either kappa or lambda), or may select different $V_L$ or $V_H$ gene segments. Different combinations of these variable region gene segments may be constructed that maintain the appropriate complementarity and reactivity with the epitope. Anti-idiotypic antibodies react with particular sections (idiotypes) of the immunoglobulin variable regions. Antibodies reactive with defined epitopes are more likely to utilize particular $V_H$ or $V_L$ gene segments than randomly selected antibodies. The particular antigenic determinant or "epitope" within the variable region that is defined by an anti-idiotype antibody is known as an idiotope. Thus, many idiotopes exist within immunoglobulin variable light and variable heavy chain segments, or are defined by three dimensionally contiguous regions of heavy and light chains.

Because of the tremendous diversity generated within the immunoglobulin gene system, cross-reactivity of anti-idiotypes rarely is seen and not expected. In cases where different antibody molecules are reactive with the same antigenic determinant (epitope), cross-reactive idiotypes are more frequently observed. This is based on the need to select appropriate $V_L$ and $V_H$ gene segments that would have a complementary structure to the antigenic determinant (epitope). Thus, the finding of shared anti-idiotypes suggests that these antibody molecules may be reactive with similar epitopes (in the immunoglobulin case, idiotopes). However, similar $V_L$ and $V_H$ gene segments may be used for reactivity to other antigenic determinants. In these cases, anti-idiotypes may cross-react with antibodies that do not have similar antigen binding specificities. Thus, the discovery by the inventor that lymphomas have shared idiotopes suggests that either these idiotopes are reactive with similar antigenic determinants (for example, antigens associated with pathogenesis) or that the malignant B-cells are pre-disposed to select particular $V_H$ or $V_L$ gene segments in the malignant process.

Antibodies are only one component of the animal immune response system. Whenever antibodies bind to foreign protein, they effectuate a wide range of events that may eventually lead to the destruction of the recognized antigen. Antibodies are manufactured by B-cells, which are a type of lymphocyte. A B-cell carries a sample of the particular antibody which that cell manufactures on its cell surface. As previously discussed, stimulation of this cell surface antibody by binding of an antigen will stimulate the B-cell to differentiate into a plasma cell that secretes serum antibodies in a positive feedback loop. For example, when an antigen is introduced into the bloodstream, it may come into contact with existing circulating serum antibodies. In such a case, the antigen would not reach the particular B-cell and would not cause such stimulation and differentiation. However, if the antigen introduced is in excess of the available circulating antibody, then stimulation of further antibody production can occur through this mechanism.

Immune Disease and Immunotherapy

B-cells are antibody producing cells, each expressing a different antibody its surface. The human body has the potential to express an enormous number of antibodies (i.e., $10^7$ to $10^8$). One type of cancer resulting from proliferation of a particular B-cell is a B-cell lymphoma. As a result of the diversity of B-cells, it is unexpected that any two or more B-cell lymphomas would express the same antibody idiotype on their cell surfaces.

Acquired Immune Deficiency Syndrome ("AIDS") is a fatal disease caused by the HIV virus that is often accompanied by opportunistic infections and cancers, such as B-cell lymphomas. In AIDS, these lymphomas generally are high grade lymphomas and have a poor prognosis due to their rapidly progressive clinical course, with most patients not surviving more than six months. As with B-cell lymphomas generally, cell surface antibodies produced by AIDS associated B-cell lymphomas are expected to be diverse in character. Thus, it is unexpected that these antibodies would share antigenic determinants (known as idiotopes) with each other.

In B-cell lymphoma, malignant B-cells, like their normal counterparts, express unique idiotypic determinants on their surface that may be exploited as "tumor-associated antigen" markers for immunotherapy. (See Stevenson G.T., et al., *Nature* 254:714 (1975); Stevenson, G.T., et al., *Fed. Proc.* 36:2268 (1977).) The activity of anti-idiotypes in B-cell lymphoma therapy has been demonstrated in several animal models. (See, e.g., Haughton, et al., *J. Immunol.* 121:2358 (1978); Krolick, K.A., et al., *J. Exp. Med.* 155:1797 (1982); Maloney, D.G., et al., *Hybridoma* 4:191 (1987); Stevenson, F.K., et al., *J. Immunol.* 130:9709 (1983); Parek, Y., et al., *J. Immunol.* 131:1600 (1983); Stevenson, F. K., et al., *Br. J. Cancer* 50:495 (1980).)

The inventor, and others, have studied the activity of monoclonal anti-idiotypes for therapy of human B-cell lymphomas. In these early clinical trials, anti-idiotypes have shown reproducible anti-tumor effects with most patients achieving significant clinical responses. (See Hamblin T. J., et al., *Br. J. Cancer* 42:495 (1980); Miller, R. A., et al., *N. Eng. J. Med.* 306:527 (1982); Meeker, T. C., Lowder, et al., *Blood* 65:1349 (1985); Brown, S. L., Miller, R. A., Horning, S. J., Czerwinski, D., Hart, S., McElderry, R., Basham, T., Warnke, R., Merigan, T. C., Levy, R., "Treatment of B-cell Lymphoma with Anti-Idiotype Antibodies Alone and in Combination with Alpha-Interferon," *Blood* 73:651 (1989); Rankin, E. M., et al., *Blood* 65:1373 (1985); and Lowder, J. N., et al., *Blood* 69:199 (1987).) Despite these encouraging results, lymphoma therapy using anti-idiotypes has been limited by several factors.

One of the inherent problems in developing effective anti-idiotype immunotherapy is the presence in the patient serum of circulating idiotypes derived from either tumor or normal B-cells that react with the administered antibody. Such circulating antibodies will neutralize administered anti-idiotype antibodies and prevent the administered antibody from reaching the tumor target, thereby blocking its therapeutic effect. Meeker et al., *Blood* 65:1349 (1985), shows that one cannot achieve an anti-tumor response if there is too high a level of circulating idiotype. Thus, one of the objects of the present invention is to develop anti-idiotypes that do not react with shared idiotypes expressed in high levels in the plasma, since this would limit the use of such an anti-idiotype in therapy.

On a more pragmatic note, the widespread and economical availability of anti-idiotype immunotherapy is limited by the current requirement for customized development of hybridomas producing anti-idiotype antibodies for each individual patient's tumor. The time required to develop an anti-idiotype on a custom basis may preclude treatment of some patients with late stage or rapidly progressing forms of disease. Additionally, the cost associated with patient customized anti-idiotype therapy may limit its application. Accordingly, it is an object of the present invention to develop anti-idiotypes recognizing shared idiotopes (shared anti-idiotypes) expressed by a relevant population of lymphomas. The development of a panel of anti-idiotype antibodies that are, collectively, capable of reacting with lymphomas in a significant proportion of patients would greatly facilitate the application of anti-idiotypes as diagnostic and therapeutic reagents in lymphoma management.

With respect to the general concept of shared idiotypes, diverse studies in animal and human systems have demonstrated numerous antibodies with cross-reactive idiotypes. Those systems included: human B-cell tumors (see Carson, D. A., et al., *Mol. Immunol.* 20:1081 (1983); Rankin, E. M., et al., *Blood* 68:430 (1986); Kunkel, H. G., et al., *J. Exp. Med.* 137:1453 (1977); Mayumi, M., et al., *J. Immunol.* 129:904 (1982); Kiyotaki, M., et al., *J. Immunol.* 138:4150 (1987); Kipps, T. J., et al., *Blood* 72:422 (1988)); murine immunoglobulin idiotypes (Makela, O., et al., *Immunol. Rev.* 34:119 (1977); cold agglutinin antibodies (Williams, R. C., et al., 161:379 (1968)); human rheumatoid factors (Kabat, E. A., et al., *Experimental Immunochemistry*, Thomas Pubs., Springfield, Ill. (1961); Pasquali, J. L., et al., *Eur. J. Immunol.* 13:197 (1983)); human anti-thyroglobulin antibodies (Matsuyama J., et al., *Clin. Exp. Immunol.* 51:381 (1983)); antibodies in patients with systemic lupus erythematosus (Solomon, G., et al., *Proc. Natl. Acad. Sci. USA* 80:850 (1983); Schoenfeld, Y., et al., *J. Exp. Med.* 158:718 (1983)); and T-cell tumors (Meuer, S. C., et al., *J. Exp. Med.* 157:705 (1983); Bigler, R., et al., *J. Exp. Med.* 158:1000 (1983)).

Stevenson, et al., attempted to identify anti-idiotypes for use in therapy against more than one B-cell lymphoma (shared anti-idiotypes). Their work suggests that anti-idiotypes reactive with idiotopes present in normal human serum would be most likely to react with shared idiotopes. By only looking at a limited number of antibodies, however, Stevenson, et al. ended up with only a few anti-idiotypes that reacted with a very small proportion of the lymphomas in the B-cell lymphomas that they were studying. The inventor's results show that reactivity of anti-idiotypes with normal human serum is not sufficient alone to predict those antibodies that will be cross-reactive with shared idiotopes. It is neither disclosed nor suggested in Stevenson, et al., that there would be many different antibodies reactive with shared idiotopes that would, in the aggregate, react with a large proportion of the lymphoma population. In the Stevenson, et al., study, approximately 15% of anti-idiotype antibodies generated against lymphoma idiotypes were found to react with a component of normal serum immunoglobulin. In the inventor's study, which is much larger, about 24% of anti-idiotypes produced against lymphoma idiotypes reacted with a minor component of normal serum immunoglobulin. Stevenson, et al., found two anti-idiotypes that each reacted with 6% (4 of 68) and 3% (1 of 39) respectively of B-cell tumor idiotypes tested. It is noteworthy that some of these idiotypes were myeloma proteins with known autoreactivity. As previously stated, in cases where different antibody molecules are reactive with the same antigenic determinant (epitope), cross-reactive idiotypes are more frequently observed. One of the anti-idiotypes from Stevenson, et al., reactive with a shared idiotope expressed on a follicular lymphoma, stained only a subset of the tumor cell population and, hence, would not be generally useful in therapy. This antibody reacted with 2 of 12 cases of follicular lymphoma; however, the second antibody did not react with any of 12 follicular lymphomas tested. The anti-idiotype antibodies that cross reacted with normal serum immunoglobulin were found to cross react with other tumor idiotypes. In the inventor's experience, only 32 out of 44 of such antibodies were cross-reactive with tumor idiotypes. Thus, reactivity of an anti-idiotype with normal serum does not alone predict or ensure reactivity with lymphomas. In contrast, the inventor's cross-reactive anti-idiotypes were selected on the basis of comprehensive staining of the tumor cell population. (FIG. 4).

Kipps, et al., *Blood* 72:422–428 (1988), studied surface antibodies associated with chronic lymphocytic leukemia ("CLL"). CLL cells are derived from CD-5+ lymphocytes in over 90% of patients. This is different from other lymphomas such as B-cell non-Hodgkin's lymphomas ("NHL") where presumably any of the very wide variety of B-cells could be transformed to malignancy. Kipps, et al., results showed that 25% of the $V_k$ region of the cell surface antibodies in CLL were the same. Since CLL B-cells are derived from a particular subset of B-cells, i.e., those which are CD5+, it is not surprising that they are closely related. On the other hand, they found no such homology in the NHL B-cells studied. Thus, it is unexpected to find any shared idiotypes in non-CLL B-cell lymphomas. (See also Kipps, et al., *Leukemia* 2:194 (1988); Kipps, et al., *J. Exp. Med.* 167:840–852, 847 (1988).) Both Kipps, et al., *Blood* 72:422 (1988) and Kiyotaki, et al., *J. Immunol.* 138:4150 (1987), reported a high incidence of cross-reactive idiotypes expressed in chronic lymphocytic leukemia. For CLL, the high frequency expression of conserved kappa light chain variable region gene explains the high incidence of a cross-reactive idiotype. As noted by Kipps, et al., this idiotype is not expressed in high frequency in follicular lymphomas. It is likely that the cells of CLL represent a special example in that they are CD5 positive. CD5 positive cells are known to be associated with autoreactive antibodies that also possess cross-reactive idiotypes (see *Blood* 72:422 (1988)).

Autoimmune diseases such as systemic lupus erythematosus ("SLE") and rheumatoid arthritis ("RA") are associated with antibodies that react with host self antigens. Such autoreactive antibodies or autoantibodies may react with DNA, immunoglobulin constant region determinants, nuclear proteins, RNA, cardiolipin, thyroglobulin, red cell antigens, platelet antigens, or other self antigens. Antibody 16.6 is a DNA reactive autoantibody that was orginally isolated from a patient with SLE. The 16.6 antibody contains an idiotype that is frequently expressed by autoantibodies found in patients with SLE and in some patients with RA. Thus, the 16-6 idiotype is shared among patients with these diseases. Serum and tissue levels of 16.6 related idiotypes have been shown to correlate with disease activity. In the past, rabbit polyclonal anti-serum has been used to measure 16.6 idiotype concentrations. Accordingly, it is an object of the present invention to develop anti-idiotype antibodies that identify shared idiotypes associated with the 16.6 autoantibody.

Rheumatoid factors ("RF") are autoantibodies reactive with immuno-globulin constant region determinants. RFs are found associated with many autoimmune diseases but are particularly important in rheumatoid arthritis where levels of the RF autoantibody correlate with disease activity. The prior art teaches that RFs are a polyclonal mixture of many antibodies and, thus, they would not be expected to express a dominant or restricted idiotype. Therefore, it would be unusual to find a shared idiotype expressed by both lymphomas and autoantibodies with disease antigen reactivity. However, the discovery of anti-idiotype antibodies reactive with shared idiotypes in lymphoma and autoimmune disease would greatly facilitate the use of antibodies in diagnosis and therapy of autoimmune as well as lymphoma diseases. Prior to the present invention, due to the tremendous diversity of the B-cell population, an anti-idiotype antibody had to be prepared on a customized basis for use in diagnosis or treatment of lymphoma or autoimmune disease. This is difficult, time consuming, and expensive. Accordingly, it is an additional object of the present invention to develop pre-formulated anti-idiotype antibodies reactive with shared idiotopes that can be used with greater efficiency in evaluation, diagnosis, and therapy of lymphoma and/or autoimmune diseases.

Summary Of The Invention

In its broadest aspect, the present invention is based on the discovery of a panel of at least 32 anti-idiotype antibodies that react with shared idiotopes expressed in varying frequencies in different histologic subsets of B-cell lymphomas and autoantibodies associated with autoimmune disease. See Table 2. More specifically, the inventor has found that 108 out of 332 B-cell lymphoma cases (32.5%), including 35 of 116 follicular small cleaved lymphomas (30%), react with at least one out of 32 anti-idiotype antibodies. With respect to AIDS-associated lymphomas, the inventor has found that five anti-idiotype antibodies react with 12 of 15 of such lymphoma cases. See Table 3. Moreover, the inventor has identified at least seven anti-B-cell lymphoma antibodies that also binds selected autoantibodies. See Table 6. This degree of cross-reactivity is high, and certainly not predictable. The inventor discloses and claims herein these and other novel anti-antibodies that may be useful in the treatment, diagnosis and/or monitoring of autoimmune diseases, AIDS- and non-AIDS-associated lymphomas.

Detailed Description Of Preferred Embodiments

Figure 1:
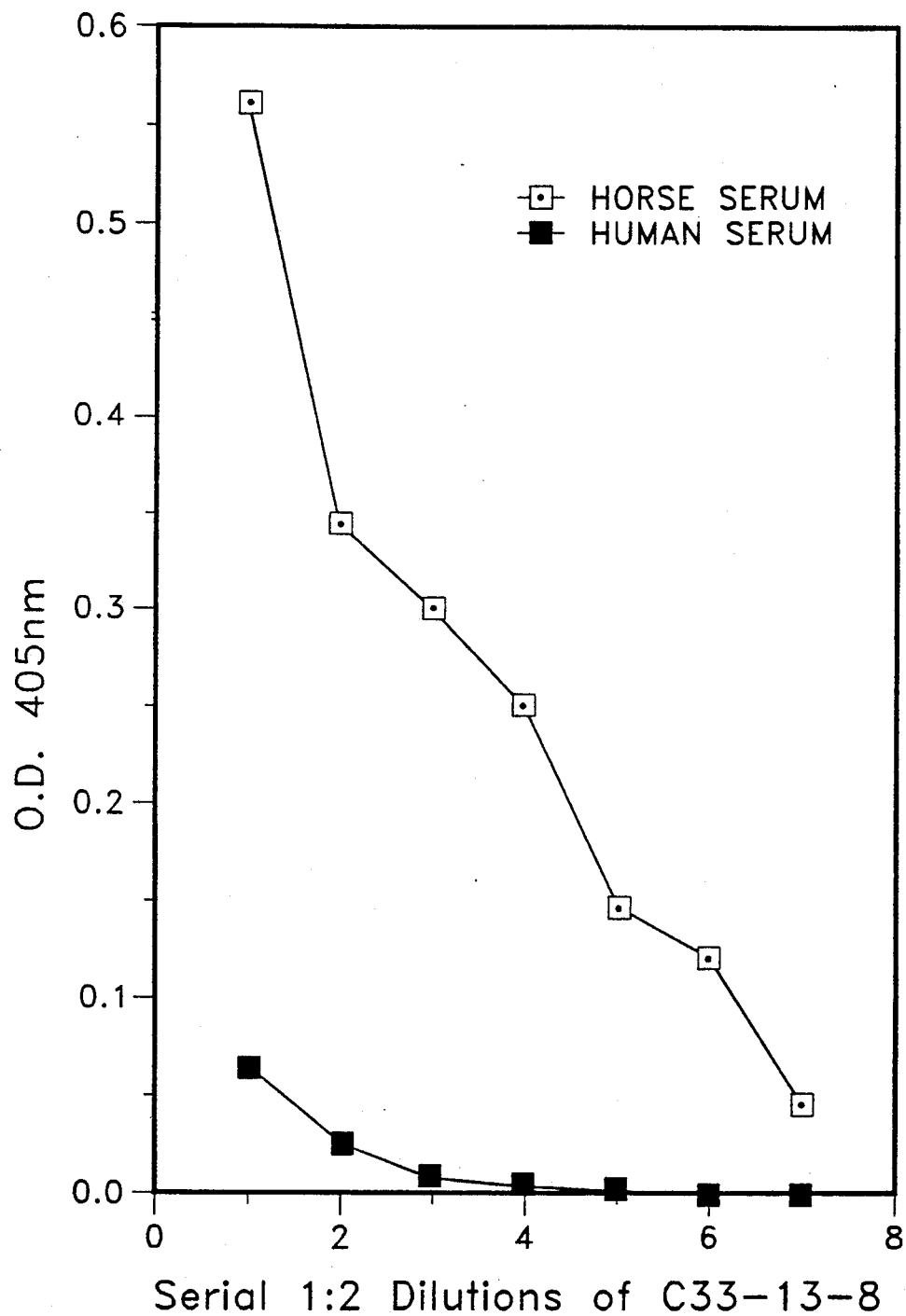
FIG. 1 shows a competitive inhibition ELISA used as the primary screen for anti-idiotype monoclonal antibodies reactive with shared idiotopes in normal human serum. Compared to horse serum, human serum produced a greater than four-fold inhibition of binding of monoclonal anti-idiotype antibody C33-13-8 to shared idiotope on the idiotype derived from the tumor.

The inventor has produced at least 199 monoclonal anti-idiotypes directed against the tumors of 67 patients with low grade, follicular, B-cell lymphomas. Low grade follicular B-cell lymphoma is one of the more common types of B-cell lymphomas. The diagnosis is based on clinical features and histologic appearance. To determine the frequency of anti-idiotypes recognizing shared idiotypes, the inventor screened this panel of anti-idiotypes using a modification of the technique described by Stevenson, et al., *Blood* 68:430 (1986). Using this technique, anti-idiotypes reactive with minor components of normal serum immunoglobulin were selected and examined for their cross-reactivity against a collection of lymphomas and other proteins, e.g., autoantibodies.

The inventor also has found that some anti-idiotypes produced against non-HIV associated B-cell lymphomas react with shared idiotopes expressed on non-HIV associated and HIV associated B-cell lymphomas. As previously described, the immune system has an enormous number of possible permutations, making shared idiotypes highly unlikely. The inventor has found 32 anti-idiotype antibodies capable of cross-reacting with B-cell lymphomas from 108 different patients. This data shows the potential also exists for therapy against B-cell lymphomas generally using a panel of anti-idiotype antibodies. In fact, the inventor has isolated one anti-idiotype, S37-48-6-2-6, that is capable of cross-reacting with B-cell lymphomas in 15 out of 381 patients.

Yet another aspect of the present invention is the use of these anti-idiotypes to shared idiotopes in immunotherapeutic treatment of B-cell lymphomas. As a result of the present invention, a panel of anti-idiotypes reactive to shared idiotopes can be generated, from which one or more antibodies may be used to treat a patient; this therapeutic modality address many of the problems in the prior art, which have been previously discussed. These novel antibodies have advantages over private anti-idiotypes in that they are more economical and practical to use in disease treatment, diagnosis and/or monitoring.

The inventor has also discovered that AIDS-associated B-cell lymphomas express antibodies that may be useful in active and/or passive treatment of HIV infection. The inventor has discovered that antibodies produced by these lymphomas recognize HIV antigens. The lymphoma cells can be induced, for example, by hybridoma techniques to secrete these antibodies. Antibodies so generated can then be used as passive therapy to treat HIV infection. The inventor has generated cell lines from such AIDS-associated lymphomas, the cells of which secrete human monoclonal antibodies reactive with the HIV virus. The inventor has isolated and tested one of these antibodies and have found that it reacts immunologically with the envelope glycoprotein antigen of HIV virus (gp 120). Thus, these B-cell lymphomas are a source of antibodies that react with HIV virus. Since they were derived from human monoclonal tumors, such antibodies are preferred for certain applications over the mouse monoclonal antibodies frequently employed in therapy. These human antibodies can also be used to detect and identify the HIV virus.

These antibodies produced from AIDS-associated lymphomas also can be used to produce anti-idiotype antibodies. The anti-idiotypes bear the "internal image," i.e., share certain three dimensional features with the original antigen to which the antibodies bind. Thus, these anti-idiotypes immunologically mimic the HIV antigens. They are readily available and non-toxic to humans and can elicit an immune response in the same manner as the corresponding epitopes of the original antigens without the accompanying viral threat to the patient. This immune response can act to protect the patient from infection by the real virus. In addition, by judiciously mixing various anti-idiotypes a broad immune response can be invoked in a patient that will react to many variants of the HIV virus. These anti-idiotypes as useful for vaccines and as active immunotherapeutic agents against HIV infection.

In an additional aspect of the present invention, applicant has discovered that some of the anti-shared idiotype antibodies cross-react with proteins other than those associated with B-cell lymphomas. More specifically, proteins with which the anti-shared idiotypes react include: anti-DNA autoantibodies typically associated with systemic lupus erythematosus ("SLE"); rheumatoid factor ("RF"), an autoantibody typically associated with rheumatoid arthritis; and anti-nuclear proteins autoantibodies typically associated with Sjorgren's syndrome. A preferred embodiment of the present invention is the L50-19-13 anti-shared idiotope antibody, which is cross-reactive with RF and the 16.6 autoantibody associated with SLE. Using this anti-idiotype antibody, it has been shown by the applicant that RFs in some patients have restricted idiotypes. Accordingly, the L50-19-13 antibody is useful in passive immunotherapy to modulate or downregulate the production of pathogenic autoantibodies, e.g., 16.6 and RF. In an alternative therapeutic application, solid phase immunoadsorbent devices incorporating L50-19-13 are useful in extracorporeal extraction of autoantibodies from patient plasma. Further, the L50-19-13 antibody is useful for in vitro assays useful for diagnosis, prognosis and monitoring of autoimmune disease, wherein the L50-19-13 functions as the detector of autoantibodies.

With respect to SLE, the inventor has identified at least three anti-idiotype antibodies that react with various determinants within the 16.6 idiotype. These antibodies identify shared idiotypes associated with 16.6 autoantibodies.

Preparation of Idiotype

Production of tumor idiotype was accomplished according to previously described procedures. (Carrol, W. L., et al., *J. Immunol. Methods* 89:61 (1986).) Briefly, HIV associated or non-HIV associated lymphoma cells were fused with K6H6/B5 (Stanford University), a HAT sensitive heterohybridoma. Another comparable fusion partner that may be used is SP2/0 Ag 14 (ATCC Designation CRL 8287). Hybridomas secreting immunoglobulin of the same heavy and light chain immunoglobulin type as that of the patient's tumor were identified by an enzyme linked immunoabsorbent assay (ELISA). Selected wells containing these hybrids were expanded separately and were later pooled. The idiotypes were purified from cell culture supernatant by immunoaffinity chromatography.

Testing of Idiotypes from HIV Associated Lymphomas

Hybridomas produced as described immediately above, from HIV associated lymphomas were grown in tissue culture. Supernatants containing the secreted idiotype were tested for HIV binding activity by Western blotting. Western blotting was performed by incubating the supernatants with cell lysates derived from an HIV infected cell line known as H9/HTLV-IIIB (ATCC Designation CRL 8543), according to the following protocol. Extracts from H9/HTLV-IIIB cells were prepared by disrupting eighty million cells with one ml of viral disruption buffer (0.1% Triton-X 100 in PBS, pH 7.2, and 0.15 mg. diethylthiothreitol/ml). After 10 minutes at room temperature, the lysate was clarified by centrifugation for 10 minutes at 12,000 g. The supernatant was mixed 1:1 with 2×sample buffer and 0.4 ml of this mixture was fractionated by sodium doedecyl sulfate polyacrylamide gel electrophoresis (hereinafter referred to as SDS-PAGE) on a 14% slab gel. The protein bands on the gel were then transferred to nitrocellulose. After electrophoretic transfer, the blot was incubated overnight at 4° C. in blocking buffer containing 20% calf serum in PBS, pH 7.2. After blocking, the nitrocellulose sheet was placed onto slot blot apparatus (Integrated Separation Systems, Park, MA) and aligned with the channels of the blotter. 0.15 ml of hybridoma supernatant and HIV positive and negative sera (1/50 dilution is blocking buffer) was assayed for two hours at room temperature in each of the channels. The channels were subsequently washed with 200 mls of blocking buffer and the conjugated antibody, goat anti-human Ig-horse radish peroxidase (HRP) (1/250), was incubated on the blot for two hours at room temperature. The second antibody was washed with 200 mls of blocking buffer and the nitro-cellulose sheets were removed from the blocking apparatus and subjected to the substrate 4-chloronapthol. After 15 minutes at room temperature, the extent of the reactivity of the antibodies was detected by the intensity of the blue band corresponding to the molecular weight of the positive sera proteins.

Generation of Monoclonal Anti-Idiotypes

Purified idiotype obtained from each patient's tumor was used to immunize either Balb/c mice, C57/BL6 mice or Fisher 344 rats as previously described (see Thielmans, K., et al., *J. Immunol.* 133:495 (1984)). Three days following the final boost, spleen cells were fused with the non-secreting mouse myeloma cell line, SP2/0 Ag 14 (ATCC Designation CRL 8287). Ten to fourteen days following the fusion, hybridoma supernatants were tested for anti-idiotype specificity by ELISA screening with the patient's tumor idiotype and a panel of six idiotypes isolated from other patients, some of which were isotype matched. Antibodies were characterized further by testing hybridoma supernatants for reactivity against frozen tissue sections of the patient's tumor tissue and unrelated human tonsil using an immunoperoxidase staining technique. (See Thielmans, K., et al., *J. Immunol.* 133:495 (1984).) Anti-idiotypes were selected on the basis of reactivity with both the patient's idiotype and tumor tissue, but not with the panel of isotype matched immunoglobulins or tonsil (from unrelated donor). The anti-idiotype secreting hybridomas were then cloned by limiting dilution and expanded by in vitro passage. Culture supernatants or purified antibody obtained were utilized in subsequent studies.

Selection of Anti-Idiotype MAbs Reactive with Shared Anti-Idiotypes

A competitive inhibition ELISA was employed as the primary screen to identify anti-idiotypes that showed detectable binding to immunoglobulin in normal human serum. Anti-idiotypes were diluted serially and mixed with either undiluted normal human serum (pooled from 40 normal donors) or horse serum as a control. After one hour, samples were added to a microtiter plate, previously coated with the tumor idiotype, and incubated for an additional hour. Plates were washed and horseradish peroxidase conjugated goat anti-mouse immunoglobulin G (Tago Inc., Burlingame CA) was added. Bound anti-idiotype was measured by adding ABTS-hydrogen peroxide substrate, and the absorbance was measured at 405 nm by an automated ELISA plate reader. Binding to normal human serum immunoglobulin was considered significant when there was a four-fold or greater inhibition of anti-idiotype reactivity with the tumor immunoglobulin by pooled human serum compared to control horse serum.

A second screening assay was employed to quantitate the level of the shared idiotope in normal human serum. Saturating concentrations of anti-idiotypes identified by the primary screen were incubated with a range of concentrations of purified tumor idiotype and with serial dilutions of pooled normal human serum. After a one-hour incubation, these samples were added to microtiter plates coated with purified tumor idiotype. Bound anti-idiotype was measured as described above. The concentration of immunoglobulin in serum reactive with the anti-idiotype was then calculated by comparing the titration curves generated with dilutions of either the human serum or purified tumor idiotype.

Shared Idiotope Expression by B-Cell Neoplasms and Benign Hyperplastic Lymphoid Tissues Tumor specimens were derived from patients with an established diagnosis of lymphoma. Histopathologic diagnoses were made using the International Working Formulation. (See "The Non-Hodgkin's Lymphoma Pathologic Classification Project Writing Committee", National Cancer Institute sponsored study of classifications of non-Hodgkin's lymphomas, *Cancer* 49:212 (1982).)

Antibodies to shared idiotopes were tested for reactivity with lymphomas and benign hyperplastic lymphoid tissues (tonsil or lymph node) by immunofluorescence and/or immunoperoxidase staining of fresh frozen cryostat sections or cell suspensions. (See Thielemans, K., et al., *J. Immunol.* 133:495 (1984); Samoszuk, M. K., et al., *Hybridoma* 6:605 (1987).) Immunofluorescence staining of cell suspensions was analyzed either by fluorescence microscopy or flow cytometry using a fluorescence activated cell sorter (FACS 440, Becton Dickinson, Mountain View, CA). Surface immunoglobulin (immunoglobulin) expression was determined by staining with fluorescein conjugated, goat anti-immunoglobulin heavy or light chain reagents (Tago). Idiotype expression was determined by indirect immunofluorescence staining using a fluorescein conjugated, goat anti-mouse immunoglobulin (Tago) reagent in a second step.

Generation of Anti-Idiotype Antibodies

One to five anti-idiotypes were developed for each of 67 B-cell lymphoma patients. One hundred ninety-nine (199) monoclonal antibodies were produced from over 60 fusions (Table 1). These monoclonal antibodies were specific for the immunizing idiotype and were non-reactive with a panel of six other lymphoma-derived idiotypes. The 199 monoclonal antibodies were selected both because of their idiotypic specificity and comprehensive reactivity with the tumor cell population in the patient's biopsy specimen.

Screening Anti-idiotypes for Reactivity to Shared Idiotopes

The initial screening assay was designed to identify anti-idiotypes that cross-reacted with normal human serum. A representative assay is shown in FIG. 1 using the anti-idiotype designated C33-13-8. Undiluted normal human serum (but not the horse serum control) was able to inhibit the binding of anti-idiotype to its corresponding shared idiotope on the tumor idiotype. An anti-idiotype reactive with a private determinant present on this tumor idiotype was not inhibited by either human or horse serum. (Data not shown). Using this assay, 152 anti-idiotypes (76%) were found to be completely non-reactive with pooled normal human serum. Such anti-idiotypes recognize private determinants expressed on the corresponding patient's lymphoma that are not present in pooled normal serum. Forty-seven of the 199 MAbs (24%) were found to react with shared idiotopes present in pooled normal human serum immunoglobulin. (Table 1).

TABLE 1

SELECTION OF ANTI-IDIOTYPE ANTIBODIES RECOGNIZING SHARED IDIOTOPES EXPRESSED ON LYMPHOMAS

| | No. of MAbs[1] | No. of Patients[1] |
|---|---|---|
| Anti-idiotypes Used | 199 | 67 |

TABLE 1-continued
SELECTION OF ANTI-IDIOTYPE ANTIBODIES RECOGNIZING SHARED IDIOTOPES EXPRESSED ON LYMPHOMAS

| | No. of MAbs[1] | No. of Patients[1] |
|---|---|---|
| in Study | | |
| Initial Screening[2] | 47 | 31 |
| Selected for Screening on Tissue[3] | 37 | 26 |
| Positive on Another Lymphoma Idiotype | 21 | 19 |

[1]Number of monoclonal antibodies and number of lymphoma patients from which idiotypes were derived, respectively.
[2]Number of anti-idiotypes reactive with pooled normal human serum (40 donors).
[3]Ten antibodies were excluded from further analysis because of poor hybridoma antibody secretion rates.

Figure 2:
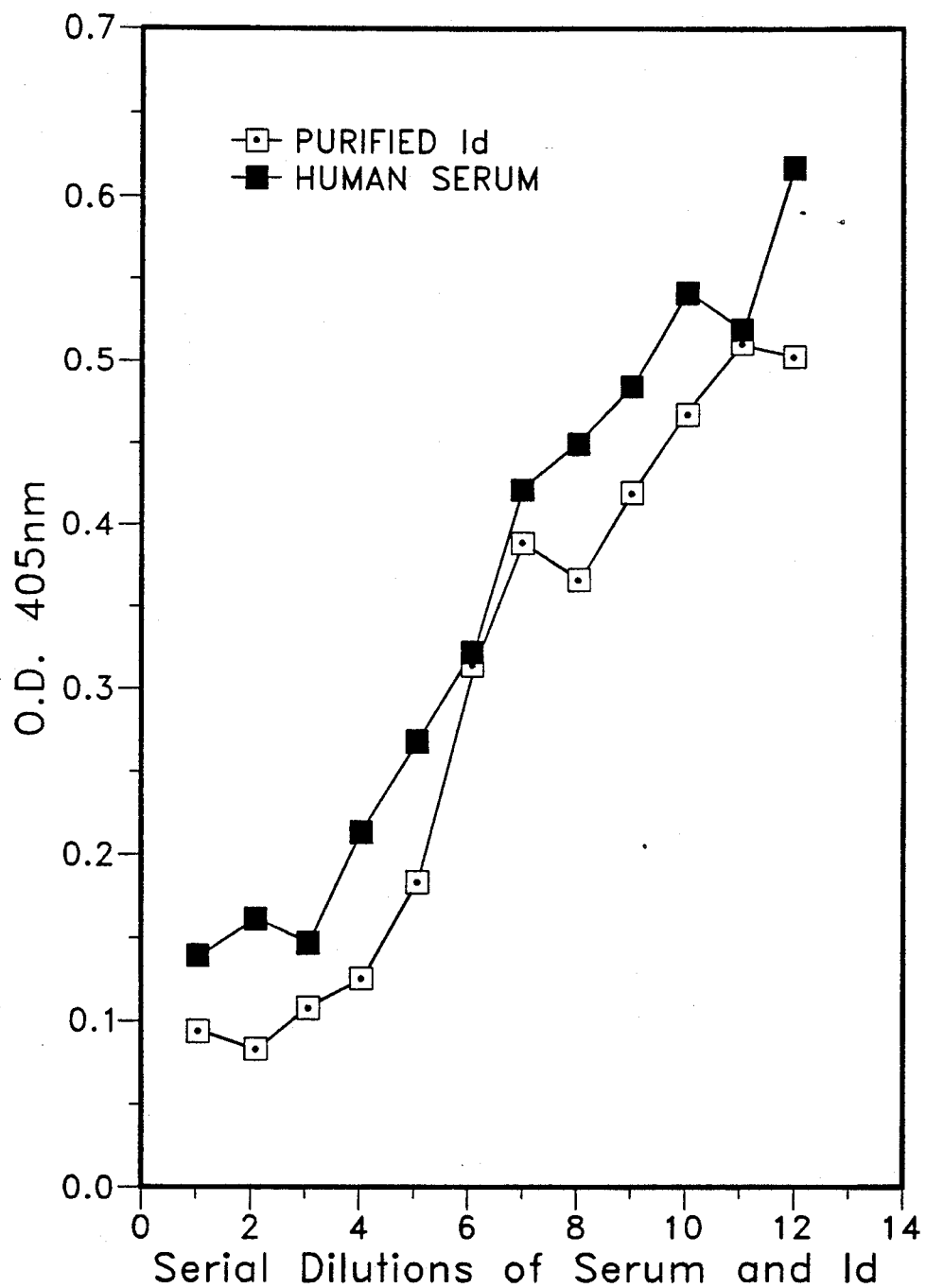
FIG. 2 shows a second-stage quantitation assay of anti-idiotype binding to immunoglobulin in pooled human serum. Serial dilutions of anti-idiotype C33-13-8 with pooled human serum generate a curve that is similar to the competitive inhibition curve produced by incubation of C33-13-8 monoclonal antibody with serial dilutions of purified idiotype at a starting concentration of 25 μg/ml. Comparison of the midpoints of the curves reveals a concentration of immunoglobulin bearing the shared idiotope in serum calculated to be 32 μg/ml.

As a second step in the screening process, the inventor determined the quantitative level of shared idiotope in normal human serum. A representative example of this assay is shown in FIG. 2 and summarized in Table 2.

TABLE 2
REACTIVITY OF ANTI-SHARED IDIOTYPES WITH NORMAL SERUM, BENIGN LYMPHOID HYPERPLASIA AND LYMPHOMAS

| Hybridoma Clone | Concentration of Shared Idiotopes in Normal Serum (ug/ml) | Reactivity of Anti-Shared Idiotopes With: Benign Lymphoid Tissue[2] | Lymphomas, % positive[3] |
|---|---|---|---|
| S37-48-6-2-6 | N.D.[1] | <5% | 15/381, 3.9% |
| J18-76-6 | N/A | <5% | 1/28, 3.6% |
| C31-145-12 | 20 | Negative | 13/363, 3.6% |
| S2-33-8 | 16 | <5% | 10/353, 2.8% |
| C33-13-8 | 32 | Negative | 9/363, 2.5% |
| C33-23-7 | N/A | N/A | 9/363, 2.5% |
| W20-66-1 | N/A | Negative | 5/25, 1.9% |
| S30-47-9 | 75 | Negative | 7/380, 1.8% |
| C39-30-7 | 0.6 | Negative | 5/294, 1.7% |
| C52-22-10 | 100 | Negative | 5/287, 1.7% |
| C45-23-7 | 69.8 | Negative | 5/287, 1.7% |
| C39-25-25 | 6 | Negative | 5/294, 1.7% |
| H48-16-2 | 10 | <5% | 5/381, 1.3% |
| H27-17-11 | 26 | <5% | 5/381, 1.3% |
| L50-19-13 | 14 | Negative | 4/387, 1.0% |
| L46-49-10-3 | 19 | <5% | 4/387, 1.0% |
| S26-16 | N.D. | Negative | 3/363, 0.8% |
| W15-26-6 | N/A | <5% | 2/257, 0.78% |
| H22-10-11 | 1.7 | <5% | 2/303, 0.66% |
| B4-11-2 | 1.6 | Negative | 2/365, 0.55% |
| C22-4-4 | 3 | Negative | 2/365, 0.55% |
| B4-1-2-31 | 1.6 | <5% | 2/365, 0.55% |
| H101-2 | 160 | Negative | 2/380, 0.53% |
| W15-82-3 | N/A | <5% | 1/257, 0.39% |
| C49-15-35 | 75 | Negative | 1/287, 0.35% |
| S66-76-23-9 | 0.6 | Negative | 1/294, 0.34% |
| S71-157-10 | N.D. | <5% | 1/355, 0.28% |
| H70-9-55 | 1.9 | Negative | 1/363, 0.28% |
| H55-4-2 | 1.7 | <5% | 1/365, 0.27% |
| L50-5-14 | 40 | <5% | 1/381, 0.26% |
| H28-48-11 | 25 | Negative | 1/387, 0.26% |
| S20-26 | 13 | Negative | 1/380, 0.26% |
| S62-30 | 23 | Negative | 0/155 |
| S61-44 | 33 | Negative | 0/155 |
| H22-20 | 1.8 | Negative | 0/104 |
| H22-15 | 1.5 | Negative | 0/104 |
| H70-1 | 16 | Negative | 0/174 |
| H55-6 | 0.9 | Negative | 0/99 |
| C49-6 | 100 | Negative | 0/41 |
| C15-87-5-15 | 17 | <5% | 0/165 |
| C49-24-10 | 9.7 | Negative | 0/41 |

[1]Not done.
[2]Percent positive cells determined by immunoperoxidase staining of frozen tissue sections. Negative: no positive cells seen; <5%; rare positive cells seen.
[3]Number of positive cases/total number of cases tested. Does not include the patient whose idiotope was used to raise the anti-idiotype for which the anti-idiotype was developed.

Blocking of anti-idiotype binding to its corresponding, purified tumor idiotype by human serum was compared to the blocking of anti-idiotypes by horse serum. Mab C33-13-8 was found to react with 32 µg/ml of immunoglobulin bearing shared idiotope present in normal human serum. Forty-seven monoclonal antibodies were found to react with shared idiotopes in human serum present in levels from 0.6 µg/ml to 160 µg/ml. Of these 47 anti-idiotypes, 90% reacted with <50 µg/ml and 78% reacted with <25 µg/ml of the shared idiotope. Thirty-seven hybridomas were selected for further analysis. (See Tables 1, 2.)

Identification of Anti-idiotypes Reactive with Shared Idiotopes Expressed in Patients with AIDS Associated B-Cell Lymphoma The inventor has found that 12 of 15 tested AIDS associated lymphomas react with five anti-idiotype antibodies. These anti-idiotypes have been deposited with the ATCC, Rockville, MD, under accession numbers: S2-33-8, ATCC #HB9981; L50-19-13, ATCC #9977; S30-47-9, ATCC #HB9980; B4-11-2, ATCC #9984; S37-48-6-2-6, ATCC #HB10009. Applicant also has deposited the patient idiotype producing hybridoma pairs that were used to select hybridomas producing anti-idiotypes reacting with shared idiotopes. S2-33-8 is reactive with idiotype from H21-12 (ATCC #HB9955) and J82-14 (ATCC #9953). To date, S2-33-8 is the best antibody that has been identified as reactive with shared idiotopes expressed by AIDS-associated B-cell lymphomas since it reacts with up to 50% of the cases (unpublished results). The reactivity of these anti-idiotypes with AIDS-associated and non-AIDS associated lymphomas are set forth below.

TABLE 3
ANTI-IDIOTYPE ANTIBODIES REACTIVE WITH HIV+ AND HIV− HIGH GRADE LYMPHOMAS

| | No. Positive Cases/Total | |
|---|---|---|
| | HIV+ | HIV− |
| S2-33-8 | 5/15 | 0/15 |
| L50-19-13 | 3/15 | 0/15 |
| S30-47-9 | 2/15 | 0/15 |
| B4-11-2 | 1/15 | 1/15 |
| S37-48-6-2-6 | 1/15 | 0/15 |
| TOTAL: | 12/15 (80%) | 1/15 (13%) |

Reactivity of high-grade AIDS-associated lymphomas with these five antibodies is associated with HIV infection since non-HIV high grade lymphomas tested were less reactive (only 1 of 15 reacted).

The unexpected, high degree of idiotype restriction seen in the idiotypes expressed in HIV associated lymphomas suggests reactivity with a common antigen. This, in turn, suggests that the lymphomas are produced by the body in response to the presence of particular HIV viral antigens (i.e., the lymphomas are antigen driven). Likewise, it is possible that non-HIV associated lymphomas may also be antigen driven. For this reason, idiotypes isolated from two HIV associated lymphomas were tested for reactivity with HIV. In one case the idiotype was found to react with the gp 120 protein isolated from HIV as determined using a Western blotting technique. (Data not shown.)

The inventor's results are unexpected because of the enormous number of different B-cells within the body. The inventor's result suggests that AIDS lymphoma B-cells might react with a common antigen. The idiotype from one of these cases was isolated and examined for reactivity with HIV. This idiotype was found to react with the HIV envelope glyco-protein (gp 120). Since the cell line producing this idiotype may be cloned and expanded in vitro, it is a source for human monoclonal anti-HIV antibody. This human monoclonal antibody has several advantages over other types of antibodies that may be raised to HIV. For example, mouse monoclonal antibodies may be produced to HIV virus. However, these will suffer from several problems when used in vivo for immunotherapy of HIV infection. The major limitation of mouse monoclonal antibodies for therapy will be their immunogenicity, as they elicit anti-mouse antibody responses in humans. Once a human anti-mouse antibody response has occurred, therapeutic effectiveness of the administered antibody is eliminated. A human monoclonal antibody would be far less immunogenic and would not result in any neutralizing antibodies produced by the host. In addition, human antibodies are capable of mediating other host effector mechanisms that are not mediated by mouse monoclonal antibodies such as the ability to fix human complement or mediate antibody dependent cell mediated cytoxicity.

Based on this invention, one can establish cell lines or produce hybridomas derived from AIDS associated B-cell lymphomas. Such antibodies, may be administered passively to treat established HIV infection, as has been done recently by Jackson, et al., *The Lancet* Sep. 17, 1988:647 (1988), using immune serum derived from HIV sero-positive asymptomatic individuals, or to prevent sero conversion in an individual exposed to HIV. Other uses for human monoclonal antibodies reactive with HIV include passive immunotherapy in patients who recently have been exposed or infected with HIV as a means of preventing disease. These anti-HIV monoclonal antibodies may also be used for production of anti-idiotype antibodies. Anti-idiotype antibodies may be produced that mimic epitopes on the corresponding HIV antigens. Such anti-idiotypes may be used in active immunotherapy to stimulate anti-HIV immune responses. These anti-idiotypes may be formulated with carrier proteins and immunologic adjuvants to augment antibody responses reactive with HIV.

Some examples of the use of monoclonal anti-HIV antibodies in passive immunotherapy are described below. One could administer the human monoclonal anti-HIV antibodies in doses ranging from 5 mgs to 500 mgs by intravenous infusion over 30 minutes to four hours (higher doses generally requiring longer infusion times). Levels of anti-HIV antibody in the plasma could be monitored to adjust the dosage and frequency of administration to achieve persistent circulating anti-HIV antibody and simultaneously measure HIV antigens, looking for disappearance of viral proteins. Doses of anti-HIV antibody could be repeatedly given to achieve persistent antibody excess and penetration into HIV infected tissues. Such dosage regimens could be applied over a period of weeks or months in either patients with established infection or those who have recently been exposed to HIV.

The anti-HIV monoclonal antibodies isolated from AIDS lymphoma cells can be used as immunogens to generate "internal image" anti-idiotype antibodies. Such anti-idiotypes can be produced in mice using established hybridoma techniques. These internal image anti-idiotypes could be covalently linked to carrier proteins and used with immunological adjuvants to boost immune responses. 0.5 to 10 mg of anti-idiotype could be given subcutaneously or intramuscularly. Such patients after repeated immunizations would produce neutralizing immunoglobulins that would be similar to anti-HIV antibodies produced by some individuals upon exposure to HIV. These anti-idiotype vaccines or immunotherapeutic agents would have a role in prevention of HIV infection and/or treatment of established disease, respectively.

Still other uses for the anti-idiotype antibodies directed against AIDS B-cell lymphoma idiotypes involve passive immunotherapy of B-cell lymphomas that arise in these patients. Doses up to 500 mgs could be given intravenously over up to several hours achieving antibody excess and penetration of anti-idiotype into lymphoma tissue. Penetration of anti-idiotype into tissue has been associated with tumor responses in other types of human B-cell lymphomas.

Because of the availability of pre-existing anti-idiotypes for these patients, one can use anti-idiotypes earlier in the treatment course, as the necessity of making a customized anti-idiotype has been eliminated. To practice this invention in diagnosis, tumor cells from patients with HIV or non-HIV associated lymphoma would be tested for reactivity with this panel of antibodies using either immunofluorescence or immunohistochemistry as described in applicant's methods section. The antibody or antibodies found to be reactive with the lymphoma could be used in diagnosis, monitoring and/or treatment. One can use the antibodies from the panel to monitor disease status or to treat. Obviously, the best antibody or antibodies for administration to any patient from the panel herein disclosed and claimed can only be determined by individualized testing, for example immunofluorescence or immunohistochemistry (see above), or by methods previously described (see Meeker, T. et al., *Blood* 65:1349 (1985)); or methods known to those skilled in the art.

Identification of Non-AIDS Associated Anti-idiotypes Reactive with Shared Idiotypes Expressed on B-Cell Lymphomas Forty-four anti-idiotypes reactive with shared idiotypes present in normal human serum were evaluated either on frozen tissue specimens or cell suspensions from 28 to 387 different patients with B-cell lymphomas and specimens of benign follicular hyperplasia tissue (tonsil or lymph node). In contrast to the results of Stevenson, et al. supra, 32 of these anti-idiotypes were found to cross react with other lymphomas as shown in Tables 1 and 2. Each of these anti-idiotypes reacted with 0.26% to 3.9% of the B-cell lymphomas tested (Table 2). The anti-idiotype with the most common reactivity with a shared idiotope, S37-48-6-2-6, was positive on 15 of 381 specimens tested (3.9%). The other anti-idiotypes reactive with shared idiotopes were positive on lower percentages of the cases tested.

Figure 3:
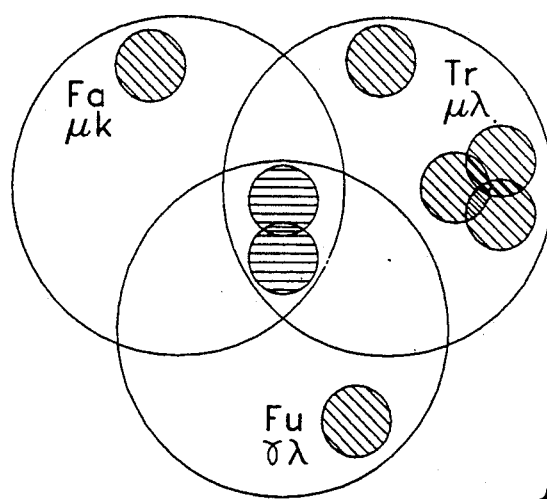
FIG. 3 uses three large circles to schematically represent the idiotype structures for patients Fa, Tr and Fu. Private idiotopes (light cross-hatched circles) and shared anti-idiotypes (dark cross-hatched circles) are indicated within the idiotype structures. Antibodies C33-13-8 and C33-23-7 define shared idiotopes expressed by tumor cells from these three patients. Other idiotopes are defined by anti-idiotypes that are private because of their lack of cross-reactivity with other patients. Overlapping small circles indicate idiotopes defined by reactivity with two or more anti-idiotype antibodies, said idiotopes being at the same or nearby positions as determined by anti-idiotype competitive binding studies.

Table 2 also shows the reactivity of each anti-idiotype with follicular hyperplasia tissue. Follicular hyperplasia is a description for the histologic appearance of lymph nodes that are being stimulated by foreign antigen. For at least 28 of the anti-idiotypes, no reactivity with these tissues was seen. The other 16 monoclonal antibodies reacted with a small percentage (<5%) of cells in the hyperplastic lymphoid tissue, i.e., rare isolated cells were seen to react with the monoclonal antibody. FIG. 3 shows an example of the reactivity with occasional cells as seen with antibody C33-13-8. For each anti-idiotype, there was no correlation between binding of the monoclonal antibody to normal pooled serum immunoglobulin or to hyperplastic lymphoid tissue and the frequency of detection of a shared idiotope expressed in the lymphomas. In contrast to non-HIV associated follicular hyperplasia, a high proportion of the cells present in follicular hyperplasia tissues isolated from some HIV infected patients react with an antibody within the disclosed panel of antibodies. Applicant's data shows that in some cases, approximately 50% of the cells were reactive with one of these antibodies (S2-33-8). In some of these cases progression to lymphoma has occurred. This suggests that these anti-ids may be useful in identifying patents with follicular hyperplasia who might progress to AIDS lymphoma.

Characteristics of the Non-AIDS Associated Shared Idiotopes

The 32 anti-idiotypes reactive with shared idiotopes identified 32 distinct determinants (idiotopes) since each of these anti-idiotypes recognized a different group of lymphomas. These anti-idiotypes have been deposited with the ATCC, Rockville, MD, having the following accession numbers: L50-5-14, ATCC #HB9973; H27-17-11, ATCC #HB9978; H48-16-2, ATCC #HB9979; S37-48-6-2-6, ATCC #HB10009; H28-48-11, ATCC #HB9957; L46-49-10-3, ATCC #HB9958; S2-33-8, ATCC #HB9981; L50-19-13, ATCC #HB9977; S30-47-9, ATCC #HB9980; B4-11-2, ATCC #HB9984; B4-1-2-31, ATCC #HB9974; C33-13-8, ATCC #HB9985; C31-145-12, ATCC #HB9983; H22-10-11, ATCC #HB9982; C39-25-25, ATCC #HB9951; S66-76-23-9, ATCC #HB9954; C49-15-35, ATCC #HB9975; C49-24-10, ATCC #HB9952; C19-87-5-15, ATCC #HB9976; C45-23-7, ATCC #HB9950; C52-22-10, ATCC #9956; W15-26-6, ATCC #HB 10347; C33-23-7, ATCC #HB10346; J18-76-6; ATCC #HB10329; W20-66-1, ATCC #HB10338; H101-2-1, ATCC #HB10331; C22-4-4, ATCC #HB10330; W15-82-3, ATCC #HB10327; H70-9-55, ATCC #HB10337; S26-16-1, ATCC #HB10328; C39-30-7, ATCC #HB10340; S71-157-10, ATCC #HB10336; H55-4-2, ATCC #HB10335; and S20-26, ATCC #HB10339. The shared idiotopes identified by these anti-idiotypes could be used to group these lymphomas into distinct families as shown in FIG. 3. These diagrams schematically demonstrate expression of the shared idiotopes relative to idiotopes defined by private anti-idiotypes produced for these patients. The inventor also has deposited the patient idiotype producing hybridoma pairs that were used to select hybridomas producing anti-idiotypes reacting with shared idiotopes. C33-13-8 is reactive with idiotype from H124-8 (ATCC #HB10010) and C18-1 (ATCC #HB10008). C33-13-8 and S2-33-8 are several of the preferred anti-idiotype antibodies in terms of frequency of reactivity with lymphoma. As previously noted, the patient idiotype producing hybridoma pairs for S2-33-8 also have been deposited.

Both the immunophenotypes and the histologic subtypes of the lymphomas expressing shared idiotopes are shown in Table 4. In seven cases the shared idiotopes were expressed by tumor idiotypes using two different immunoglobulin heavy chains, in eight cases, the shared idiotopes were expressed by tumor idiotypes using either kappa or lambda immunoglobulin light chain. The remaining anti-idiotypes identified shared idiotopes present on restricted immunoglobulin classes but only small numbers were available for analysis. The expression of shared idiotopes by immunoglobulins with different heavy and/or light chains rules out the possibility that these anti-idiotypes were recognizing allotypic or isotypic determinants.

TABLE 4

CHARACTERISTICS OF SOME OF THE SHARED CROSS-REACTIVE ANTI-IDIOTYPES

| Cross-reactive anti-idiotype defined by MAb | No. of Patients[1] | Immunoglobulin Isotypes[2] | Histologies |
|---|---|---|---|
| S2-33-8 | 11 | 6MK, 1GL, 2K, 2N.D.[4] | 5FSC; 4SNC 1DSC; 1DLC |
| S37-48-6-2-6 | 15 | 3MK, 8ML, 1GL, 3ND | 2FSC, 4SCL, 2FML, 4DSC, 1SNC, 1DML 11BL |
| S30-47-9 | 7 | 4GL, 2GK, 1G | 2FSC, 2FML, 1FLC, 1DSC, 11B |
| H48-16-2 | 5 | 2MK, 1GK, 1K, 1ML | 4FSC, 1DSC |
| C33-13-8 | 9 | 3MK, 3ML, 1GL, 1K 1ND | 3FSC, 2FML, 1FLC, 3SCL |
| C31-145-12 | 13 | 4MK, 1K, 3ND | 9FSC, 1DSC 1DML, 2SCL |
| L50-19-13 | 4 | 1MK, 1ML, 2K | 1DML, 1SNC, 2SCL |
| B4-11-2 | 2 | 1MK, 1L | 1BL; 1SNC |
| L46-49-10-3 | 4 | 2MK, 1K, 1L | 1SNC, 3SCL |
| L50-5-14 | 1 | 1MK | 1FML |
| H22-10-11 | 2 | 2MK | 1FSC, 1FML |
| S66-76-23-9 | 1 | 1MK | 1FSC |
| C39-25-25 | 5 | 1MK, 1GL, SND | 2DSC, 3SCL |

[1]Number of cases expressing the shared idiotope, including the patient for whom the anti-idiotype was developed.
[2]Immunoglobulin isotypes. Entries in bold type denote phenotype of lymphoma against which anti-idiotype was developed. M = IgM; G = IgA; K = kappa; L = lambda.
[3]Histologic subtypes of lymphomas expressing shared idiotopes. FSC = follicular, small cleaved cell; SNC = small, non-cleaved cell; DSC = small cleaved cell type, diffuse; SCL = small cell (CLL); DLC = large cell type, diffuse.
[4]Not done.

Table 5 summarizes the expression of shared idiotopes by the various histologic subtypes of non-HIV associated B-cell lymphomas. The shared idiotopes defined by these monoclonal antibodies do not appear to be restricted to a particular histologic subtypes of lymphoma. Although the number of cases that are not follicular small cleaved cell lymphomas is small, there is a suggestion that the different histologic subtypes vary in their frequency of expression of shared than seen in CLL or AIDS associated lymphomas. The inventor identified multiple shared idiotopes but each one is expressed in low frequency in the follicular lymphoma population (Table 2). In contrast to CLL, the follicular lymphoma shared idiotopes do not appear to be associated with any immunoglobulin heavy or light chain type. Interestingly, these lymphomas may be grouped into families based on their shared idiotope expression.

The findings that shared idiotopes do exist in various subtypes of B-cell lymphomas has important implications for immunotherapy using anti-idiotypes. Anti-idiotypes could be available (and ready for immediate use) at the time of tumor diagnosis and/or at relapse. Under these conditions, the practicality of using anti-idiotypes in diagnosis and treatment is enhanced. Currently, a panel of 20 anti-idiotypes reacts with, in aggregate, about 30% of follicular lymphoma idiotypes. With the availability of this panel of anti-shared idiotopes, the inventor can immunophenotype the tumor (idiotyping)

and select the appropriate antibody or combination of antibodies for use in diagnosis or therapy.

There might be other advantages to anti-idiotypes directed against shared idiotypes. For example, an important reason for tumor escape from therapy with anti-idiotypes is related to selection of idiotype negative, immunoglobulin positive variant cells. These cells arise because of extensive somatic mutation of immunoglobulin variable region genes (Meeker, T. et al., *New Eng. J. Med.* 312:165 8 (1985)). It is possible that shared idiotopes may not mutate as frequently as other segments within the variable region. This has been shown to be the case for the Vk IIIb gene of CLL Kipps T. J., et al., *J. Exp. Med.* 167:840 (1988). If shared idiotopes do not mutate as readily as other idiotopes then therapy with anti-idiotypes reactive with these determinants may be more effective.

Anti-idiotypes to shared idiotopes may be generated and selected using the techniques described herein. Large numbers of anti-idiotypes must be generated in order to find those that identify shared idiotopes. Moreover, therapeutically useful anti-idiotypes must meet certain other criteria to be useful in vivo. For example, the amount of cross-reactive idiotype present in serum must be less than 50 µg/ml in order for administered anti-idiotype to achieve penetration into tissues (see Meeker, et al., *Blood* 65:1349 (1985)). Another important factor is the proportion of cells within the tumor expressing the shared idiotope and reacting with the shared anti-idiotype. The inventor has purposely selected anti-idiotypes reacting with a high proportion (>85%) of the cells in the tumor since immunotherapy is the inventor's major objective.

Method of Screening Anti-Shared Idiotype Antibodies for Reactivity with Autoantibodies Autoantibodies, e.g., anti-DNA and RF antibodies, may be isolated from patients with SLE and RA using a heterohybridoma technique as previously described. Briefly, blood lymphocytes from patients with SLE are fused to a myeloma cell partner and the resulting hybridomas are screened for secretion of antibodies reactive with DNA or other antigens using conventional immunoassay techniques known to those of ordinary skill in the art. One can also isolate autoantibodies from serum of patients using immunoaffinity chromatography techniques.

Autoantibodies are then tested for reactivity with the applicant's panel of anti-shared idiotype antibodies using conventional ELISA techniques. Briefly, the anti-idiotype antibody is used to coat a microtiter plate. The autoantibody or control antibodies are then added to the wells at various dilutions. After washing the wells, enzyme labeled anti-id is added to the wells to detect the bound autoantibody.

Figure 7:
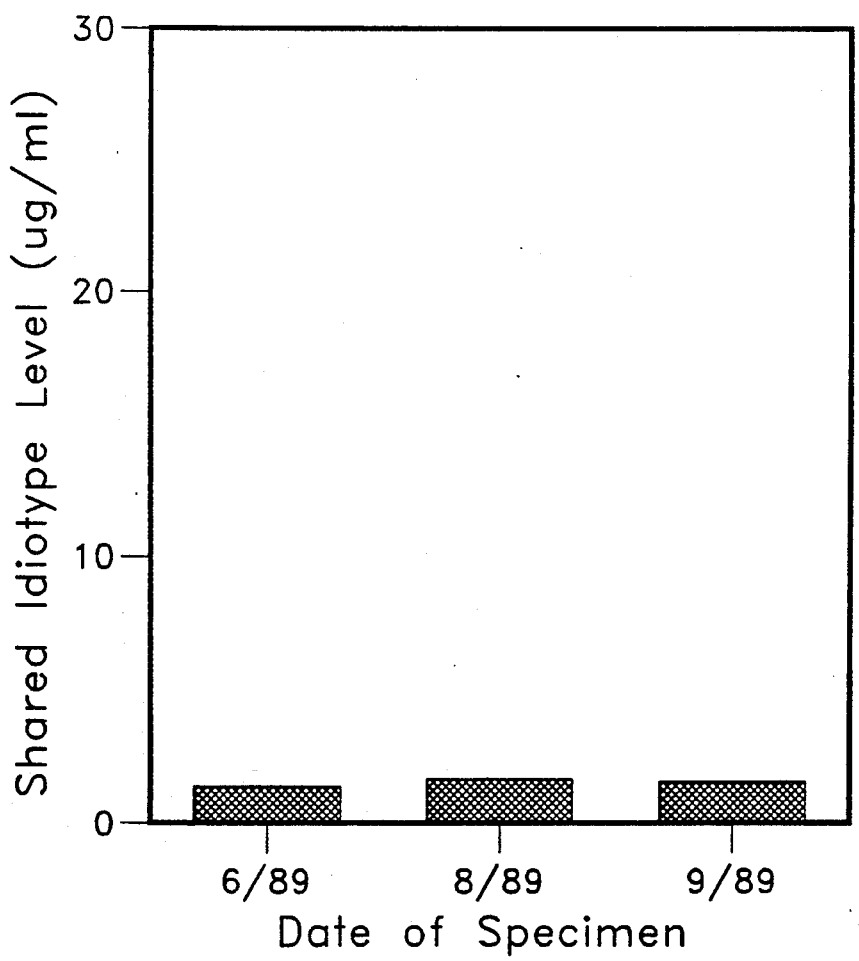
FIG. 7 depicts the level of the L50-19-13 shared idiotype over time in a patient C with rheumatoid arthritis and the correlation of idiotype level to disease progression and remission.
Figure 4A:
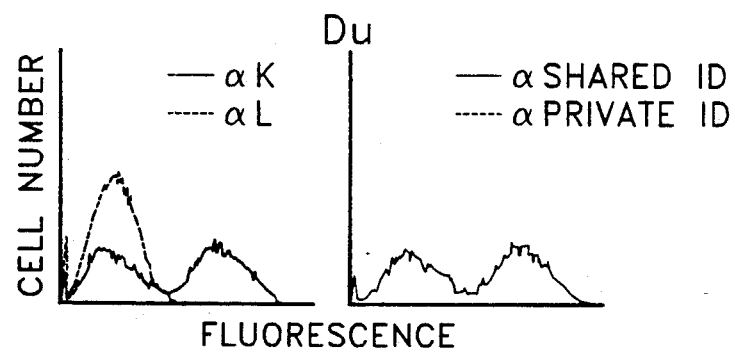
FIGS. 4A–4D are graphs showing the results of immuno fluorescence staining and FACS analysis performed using tumor cells from patients Du(IgMK), Me(IgGK), St(IgML), and Ei(IgML). The immunoglobulin bearing cells were identified by staining with anti-immunoglobulin light chain reagents which illustrate total B-cells v. that proportion of cells in the population that represented the tumor clone. Negative control staining was identical to that seen by staining with the inappropriate light chain reagent. S37-48-6-2-6 (anti-shared-idiotope) reacted with cells from patient Du, St and Ei. Tumor cells from patients St and Ei also were stained with private anti-idiotypes. S37-48-6-2-6 did not react with patient Me cells.
Figure 4B:
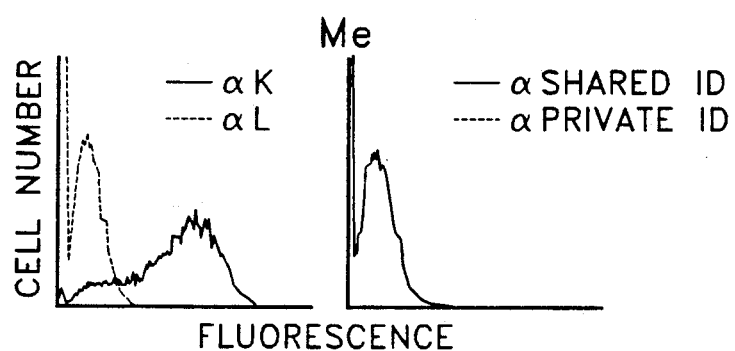
Figure 4C:
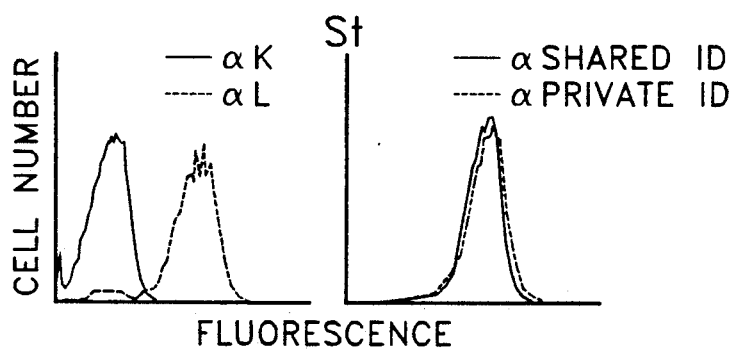
Figure 4D:
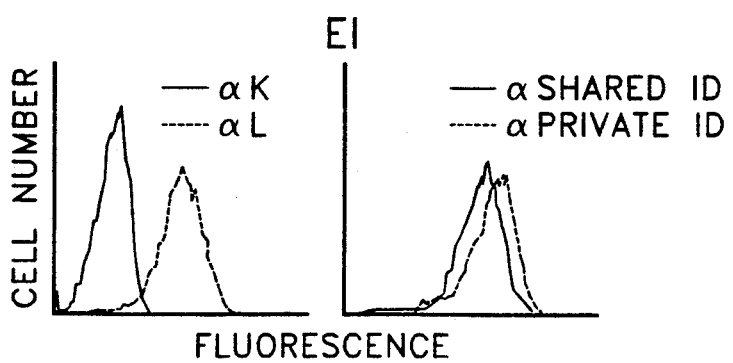
Figure 5:
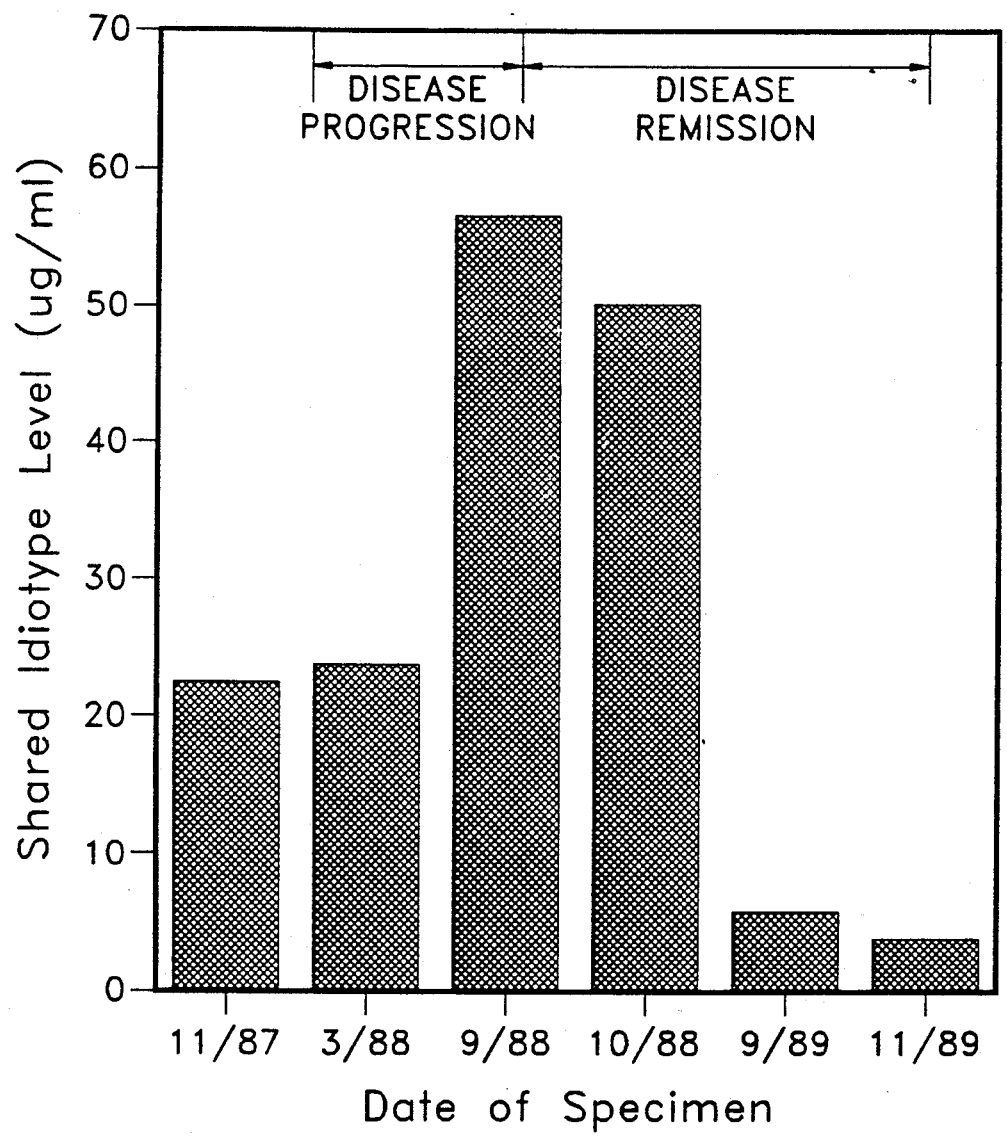
FIG. 5 depicts the level of the L50-19-13 shared idiotype over time in a patient A with rheumatoid arthritis and the correlation of idiotype level to disease progression and remission.
Figure 6:
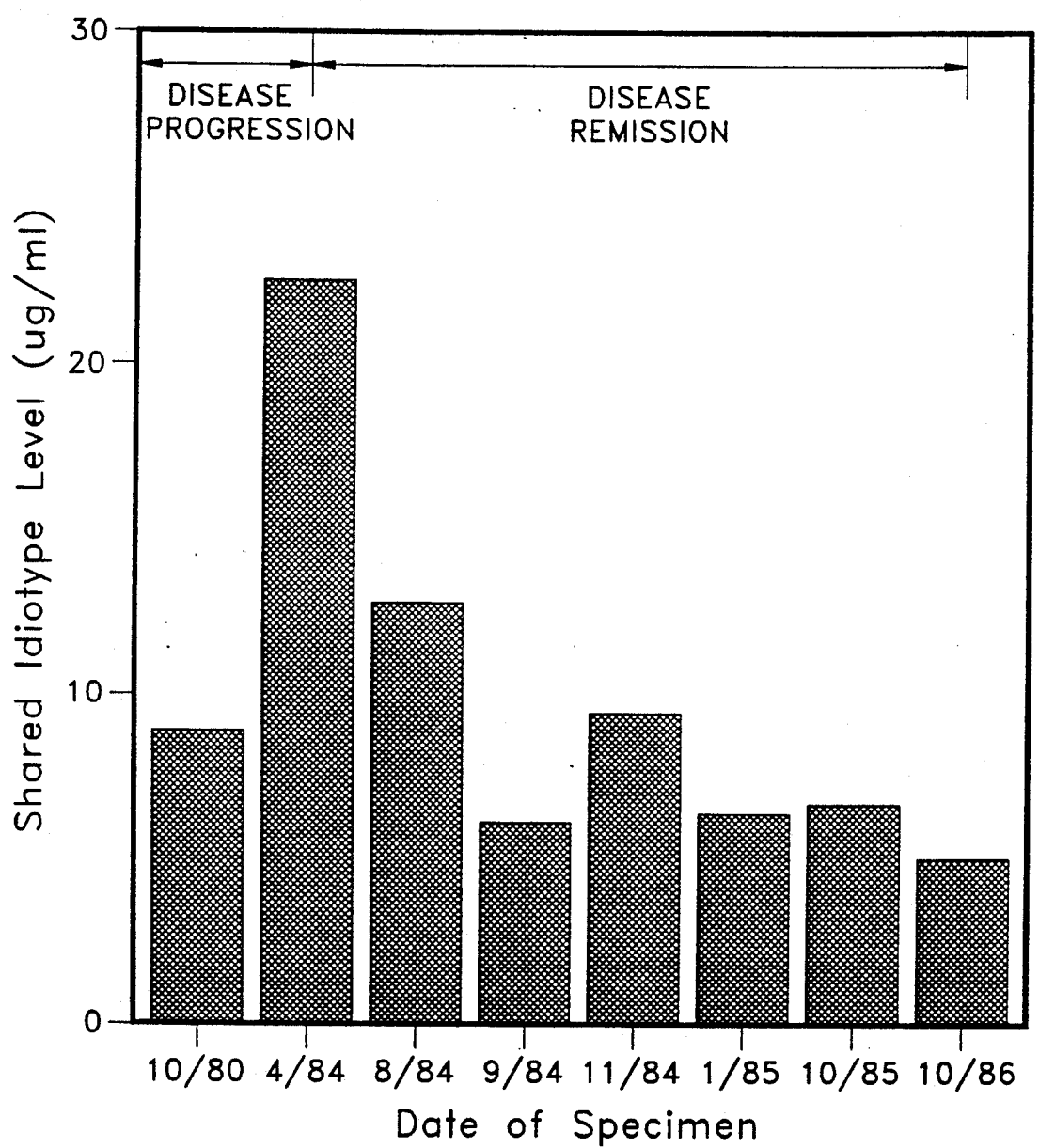
FIG. 6 depicts the level of the L50-19-13 shared idiotype over time in a patient B with rheumatoid arthritis and the correlation of idiotype level to disease progression and remission.

The anti-shared idiotype antibodies discovered by the applicant are listed in Table 6. The clinical correlation of the L50-19 idiotype level in rheumatoid arthritis and the disease progression and remission are depicted in FIGS. 5-7.

TABLE 6

| ANTI-SIDS REACTIVE WITH AUTOANTIBODIES | |
| --- | --- |
| Anti-SID | Reactive with Autoantibody to: |
| L50-19-13 (S002) | ssDNA |
| | RF |
| | La(SSB) |

TABLE 6-continued

| ANTI-SIDS REACTIVE WITH AUTOANTIBODIES | |
| --- | --- |
| Anti-SID | Reactive with Autoantibody to: |
| C31-145-12 (S006) | Cardiolipin |
| | ssDNA |
| | SmRNP |
| | PolydT |
| H101-2 | ssDNA |
| L46-49-10-13 (S015) | ssDNA |
| H70-9-55 (S009) | La |
| BE0015-1 | La |
| C15-87 | PolydT |

Once continuous cell lines, i.e., hybridomas, are screened for the appropriate antibody production, the anti-shared antibodies reactive with autoantibodies can be utilized for in vitro methods for detecting the presence or amount of autoantibodies in fluid samples. A method for the in vitro detection of the presence of an autoantibody includes contacting a fluid sample obtained from a patient with at least one anti-idiotype antibody having specific reactivity with an autoantibody, and determining the complexing of the anti-idiotype antibody to autoantibodies of the fluid sample by means of an immunoassay. Alternatively, a quantitative measurement of the amount of autoantibody in a fluid sample may be made by an in vitro method including contacting the fluid sample with at least one anti-idiotype antibody having specific reactivity with autoantibody, determining the amount of the anti-idiotype antibody associated with the autoantibody, and correlating the amount of the association with the amount of autoantibody present in the sample.

The presence or amount of anti-idiotype antibodies associated with the autoantibody being detected can be achieved by labeling the anti-idiotype antibody with a marker that is capable of being detected. The labeled antibody used in the present invention may be provided with the same labels used in prior art immunoassays. Among these may be mentioned fluorogenic labels for detection by fluorometry, as described in U.S. Pat. No. 3,940,475, and enzymatic markers, as described in U.S. Pat. No. 3,645,090. The label may also be a radioisotope, such as $I^{125}$, using, for example, the procedure of Hunter and Greenwood, *Nature*, 144:945 (1962), or that of David, et al., *Biochemistry*, 13:1014-1021 (1974). Additionally, the label may be biotin, which may be detected by its interaction with an enzymatically labeled avidin.

One of skill in the art would appreciate that the assay methods of the present invention may be qualitative or quantitative in nature and may be employed to monitor patients undergoing therapy or in initial diagnosis of autoimmune disease. Although autoantibodies are preferably detected in fluid samples, they also may be determined in tissue samples. Fluid samples utilized according to the present invention include whole blood, serum, plasma, urine, sweat, tears and saliva. A diagnostic kit for detecting the presence or amount of autoantibodies, which includes at least one anti-idiotype specific for the autoantibody of interest, may be assembled.

Immunoassay for Detection of Idiotype Positive RF Using the L50-19 Antibody as a Detector A. Using a multichannel pipette, coat a 96 well immulon plate with Human IgG,Fc fragment(Accurate) at a concentration of 5.0 μg/ml (100 μL/well) diluted in 0.05M sodium bicarbonate, pH 9.5.

B. Moisture seal each plate with a microplate sealer and incubate overnight between 2C to 8C.

C. Wash the microplate (×5) with wash buffer(0.9% W/V NaCl 0.05% Tween-20) using the automatic microplate washer.

D Using a multichannel pipette, deliver 100 μL of dilution buffer to each well.

E Leaving the well designated A1 blank, introduce 100 μL of the test serum into a single well in first column of the microplate. In the same column, introduce 100 μL of normal pooled serum into a separate well. Using an appropriate pipette, make serial two-fold dilutions of the serum across microplate moving from left to right.

F Incubate the plate for one hour at room temperature.

G. Prepare a dilution of biotin labeled anti-shared idiotype at a concentration of 2 μg/mL in dilution buffer.

H Repeat step C.

I. Using a multichannel pipette deliver 100 μL of the anti-shared idiotype antibody to the wells where the test samples were reacted.

J. Repeat step F.

K. Prepare a 1:1000 dilution of Horseradish peroxidase conjugated Avidin(TAGO) in dilution buffer.

L. Repeat step C.

M. Using a multichannel, pipette introduce 100 μL of diluted Avidin into each of the test wells.

N. Repeat step F.

O. Prepare a 1X dilution of ABTS(2,2'-Azino-bis(3-ethylbenthiazoline-6-sulfonic acid), Diammonium Salt, Sigma Chemical.

P. Repeat step C.

Q. Using a multichannel pipette, deliver 100 μL of 1X ABTS to all of the test wells and allow the color to develop for at least 15 minutes.

R. Read the absorbance values of the plate on the microplate reader at a wavelength of 405 nm. Plot the values on graph paper and connect the points.

Interpretation of data-Compare the absorbance values to normal pooled serum and determine the positive titer. Any dilution having an absorbance which exceeds the same dilution for normal serum is considered positive.

Assay for Idiotype Positive Immune Complexes

Procedure:

A. Using a multichannel pipette, coat a 96 well immulon plate with Clq (Calbiochem) at a concentration of 15.0 μg/ml (100 μL/well) diluted in 0.05M sodium bicarbonate, pH 9.5.

B. Moisture seal each plate with a microplate sealer and incubate overnight between 2C to 8C.

C. Wash the microplate (×5) with wash buffer(0.9% W/V NaCl 0.05% Tween-20) using the automatic microplate washer.

D. Using a multichannel pipette, deliver 100 μL of dilution buffer to each well.

E. Leaving the well designated A1 blank, introduce 100 μL of the test serum into a single well in the first column of the microplate. In the same column, introduce 100 μL of normal pooled serum into a separate well. Using an appropriate pipette, make serial two-fold dilutions of the serum across the microplate moving from left to right.

F. Incubate the plate for 1.5 hours at 37C and then for 0.5 hours between 2C to 8C.

G. Prepare a dilution of biotin labeled anti-shared idiotype at a concentration of 2 μg/mL in dilution buffer.

H. Repeat step C.

I. Using a multichannel pipette, deliver 100 μL of the anti-shared idiotype antibody to the wells where the test samples were reacted.

J. Incubate the microplate for one hour at room temperature.

K. Prepare a 1:1000 dilution of Horseradish peroxidase conjugated Avidin(TAGO) in dilution buffer.

L. Repeat step C.

M. Using a multichannel, pipette, introduce 100 μL of diluted Avidin into each of the test wells.

N. Repeat step J.

O. Prepare a 1X dilution of ABTS(2,2'-Azino-bix(3-ethylbenthiazoline-6-sulfonic acid), Diammonium Salt, Sigma Chemical.

P. Repeat step C.

Q. Using a multichannel pipette, deliver 100 μL of 1X ABTS to all of the test wells and allow the color to develop for at least 15 minutes.

R. Read the absorbance values of the plate on the microplate reader at a wavelength of 405 nm. Plot the values on graph paper and connect the points.

Interpretation of Data-Compare the absorbance values to normal pooled serum and determine the positive titer. Any dilution having an absorbance which exceeds the same dilution for normal serum is considered positive.

Extracorporeal Treatment of Autoimmune Disease

The L50-19-13 antibody is covalently coupled to a solid phase support such as sepharose, cellulose of polyacrylamide, or other. Patients with active disease and a rising concentration of the L50-19-13 reactive idiotype in the plasma would be eligible for extracorporeal therapy. Blood or plasma is continuously passed over the solid phase immunoadsorption device which will remove L50-19-13 reactive idiotype from the plasma. Adsorbed plasma may be re-infused into the patient or discarded and replaced by normal plasma. One or more total plasma volume exchanges should remove a majority of the disease associated idiotype. The treatment is repeated at intervals ranging from 1 day to monthly until either the idiotype is reduced to a level which is at or below the concentration seen when disease is inactive or disease remission occurs. The idiotype level is monitored and re-treatment may be initiated when the idiotype level rises and disease progressing occurs. Removal of pathogenic autoantibodies from plasma prevents the buildup of these antibodies in tissues and reduces the severity of disease.

I claim:

1. A panel comprising at least five anti-idiotype monoclonal antibodies or antigen binding fragments, each antibody or fragment specifically binding epitope expressed by at least one cell surface immunoglobulin present on malignant B cells from at least two different patients having B cell lymphomas, wherein the aggregate percent reactivity of said panel with malignant B cells is at least 15%.

2. The panel of claim 1 comprising at least 10 anti-idiotype monoclonal antibodies or antigen binding fragments, wherein the aggregate percent reactivity is at least 20%.

3. The panel of claim 1 comprising at least 14 anti-idiotype monoclonal antibodies or antigen binding fragments, wherein the aggregate percent reactivity is at least 25%.

4. The panel of claim 3 wherein said anti-idiotype monoclonal antibodies are selected from the group consisting of: L50-19-13 having ATCC accession number HB 9977, C33-13-8 having ATCC accession number HB 9985, S37-48-6-2 -6 having ATCC accession number HB 10009, C31-145-12 having ATCC accession number HB 9983), H27-17-11 having ATCC accession number, HB9978, C52-22-10 having ATCC accession number, HB9956, C45-23-7 having ATCC accession number HB9950, W20-66-1 having ATCC accession number HB 10338, W15-82-3 having ATCC accession number HB 10327, J18-76-6 having ATCC accession number HB 10329, C39-30-7 having ATCC accession number HB 10340, C49-15-35 having ATCC accession number HB 9975, S30-47-9 having ATCC accession number HB 9980 and L46-49-10-3 having ATCC accession number HB 9958.

5. The panel of claim 1 wherein at least one of said epitopes is expressed by at least one cell surface immunoglobulin present on malignant B cells from at least two different patients having Human Immuno-deficiency Virus ("HIV") associated B-cell lymphomas or leukemias.

6. The panel of claim 5 wherein said anti-idiotype monoclonal antibodies are selected from the group consisting of: S2-33-8 having ATCC accession number HB 9985, L50-19-13 having ATCC accession number HB 9977, S30-47-9 having ATCC accession number HB 9980, B4-11-2 having ATCC accession HB 9984, and S37-48-6-2-6 having ATCC accession number HB 10009.

7. The panel of claim 1 wherein at least one of said anti-idiotype monoclonal antibodies or antigen binding fragments is defined by blocking the binding of a second antibody to two or more human monoclonal antibodies derived from malignant B cells from at least two different patients having B-cell lymphoma, wherein said second antibody is selected from the group consisting of: L50-19-13 having ATCC accession number HB9977, C33-13-8 having ATCC accession number HB 9985, S37-48-6-2-6 having ATCC accession number HB10009, C31-145-12 having ATCC accession number HB 9983, H27-17-11 having ATCC accession number HB 9978, C52-22-10 having ATCC accession number HB9956, C45-23-7 having ATCC accession number HB 9950, W20-66-1 having ATCC accession number HB10338, W15-82-3 having ATCC accession number HB10327, J18-76-6 having ATCC accession number HB10329, C39-30-7 having ATCC accession number HB10340, C49-15-35 having ATCC accession number HB9975, S30-47-9 having ATCC accession number HB 9980; L46-49-10-3 having ATCC accession number HB9958; S2-33-8 having ATCC accession number HB9985; and B4-11-2 having ATCC accession number HB9984.

8. The panel of claim 7 wherein said second monoclonal antibody is derived from malignant B cells from at least two different patients having HIV associated B cell lymphomas.

9. The panel of claim 8 wherein said second antibody is selected from the group consisting of: S2-33-8 having ATCC accession number HB 9985, L50-19-13 having ATCC accession number, HB 9977, S30-47-9 having ATCC accession number HB 9980, B4-11-2 having ATCC accession number HB 9984, and S37-48-6-2-6 having ATCC accession number HB 10009.

10. The panel of claim 1 wherein at least one of said anti-idiotype monoclonal antibodies or fragments specifically binds with the same or different shared idiotope expressed by a pair of human monoclonal antibodies, said shared idiotope being defined by specific binding with:
    a) a monoclonal antibody or a derivative of a monoclonal antibody selected from the group consisting of: L50-19-13 having ATCC accession number HB 9977, C33-13-8 having ATCC accession number HB 9985, S37-48-6-2-6 having ATCC accession number HB 10009, C31-145-12 having ATCC accession number HB 9983), H27-17-11 having ATCC accession number HB 9978, C52-22-10 having ATCC accession number HB 9956, C45-23-7 having ATCC accession number HB 9950, W20-66-1 having ATCC accession number HB 10338, W15-82-3 having ATCC accession number HB 10327, J18-76-6 having ATCC accession number HB 10329, C39-30-7 having ATCC accession number HB 10340, C49-15-35 having ATCC accession number HB 9975, S30-47-9 having ATCC accession number HB 9980 and L46-49-10-3 having ATCC accession number HB 9958; or
    b) a monoclonal antibody defined by its ability to block the binding of an antibody selected from the group consisting of: L50-19-13 having ATCC accession number HB 9977, C33-13-8 having ATCC accession number HB 9985, S37-48-6-2-6 having ATCC accession number HB 10009, C31-145-12 having ATCC accession number HB 9983), H27-17-11 having ATCC accession number HB 9978, C52-22-10 having ATCC accession number HB 9956, C45-23-7 having ATCC accession number HB 9950, W20-66-1 having ATCC accession number HB 10338, W15-82-3 having ATCC accession number HB 10327, J18-76-6 having ATCC accession number HB 10329, C39-30-7 having ATCC accession number HB 10340, C49-15-35 having ATCC accession number HB 9975, S30-47-9 having ATCC accession number HB 9980 and L46-49-10-3 having ATCC accession number HB 9958.

11. A method of immunotherapy comprising the step of administering at least one anti-idiotype antibody or antigen binding fragment from the panel of claim 1 to a patient.

12. A method of immunotherapy comprising the step of administering at least one anti-idiotype antibody or antigen binding fragment from the panel of claim 4 to a patient.

* * * * *